US00PP09055P

United States Patent [19]

Hesse

[11] Patent Number: Plant 9,055

[45] Date of Patent: Feb. 7, 1995

[54] CHRYSANTHEMUM PLANT NAMED PACIFIC ISLE

[75] Inventor: Peter S. Hesse, Nipoma, Calif.

[73] Assignee: Clearwater Nursery, Inc., Nipoma, Calif.

[21] Appl. No.: 179,040

[22] Filed: Jan. 7, 1994

[51] Int. Cl.[6] ..... A01H 5/00

[52] U.S. Cl. ..... Plt./82.4

[58] Field of Search ..... Plt. 74.1, 82.4, 82.5

*Primary Examiner*—Howard J. Locker

*Attorney, Agent, or Firm*—Arnold, White & Durkee

[57] ABSTRACT

The present invention comprises a new and distinct cultivar of Chrysanthemum, botanically known as *Dendranthema grandiflora,* and referred to by the cultivar name Pacific Isle. The new cultivar is distinguished by its lavender ray floret coloration and dark green leaves.

1 Drawing Sheet

BACKGROUND OF THE NEW PLANT

Pacific Isle was among the progeny of a cross made by Peter S. Hesse between the female parent Splendor (U.S. Plant Pat. No. 5,225) and the male parent Hopscotch (U.S. Plant Pat. No. 5,816). The cross which produced Pacific Isle was part of a controlled breeding program conducted by Peter Hesse in Nipomo, Calif.

Pacific Isle was discovered in a cultivated area and selected as one flowering plant within the progeny of the stated cross by Peter S. Hesse in November 1989, in a controlled environment in Nipomo, Calif.

The first act of asexual reproduction of Pacific Isle was accomplished when vegetative cuttings were taken in January 1990, in a controlled environment in Nipomo, Calif., by Peter S. Hesse.

Horticultural examination of controlled flowerings of successive plantings has shown that the unique combination of characteristics as herein disclosed for Pacific Isle are firmly fixed and are retained through successive generations of asexual reproduction.

Pacific Isle has not been observed under all possible environmental conditions. The phenotype may vary significantly with variations in the environment such as temperature, light intensity and daylength.

The following observations, measurements and comparisons describe plants grown in a controlled environment in Nipomo, Calif. Unrotted cuttings were directly stuck into 6.5" pots and grown under the natural temperature and daylength prevailing in January through March of 1990.

Color designations are compared to the 1986 edition of R.H.S. Colour Chart, first published in 1986 by the Royal Horticultural Society, London England. The B-NINE TM growth regulator referred to in the culturing procedures is 2,2-dimethyl hydrazide sold under the name of Daminozide or Alar and manufactured by Uniroyal.

The following traits have been repeatedly observed and are determined to be basic characteristics of Pacific Isle, which in combination distinguish this Chrysanthemum as a new and distinct cultivar.

1. Flat capitulum form
2. Daisy capitulum type
3. Lavender fully expanded outer ray florets
4. Yellow Daisy disc
5. An average of 4.6 flowers per break 6. Diameter across the face of capitulum of 11.6 cm as a disbud
7. Exceptional upright to spreading habit with an average of 4.0 breaks after a single pinch
8. Flowering response is approximately 58 days from the start of short days
9. Ease in control of plant height from the bench such that the finished height will range from 9.5–11.5 inches depending on application of growth regulators.

DESCRIPTION OF THE PHOTOGRAPH

The accompanying photograph shows typical inflorescence and leaf characteristics of Pacific Isle, with the colors being as nearly true as possible with illustrations of this type. Unrooted cuttings were pinched spray pot mum with 5 cuttings in a 6.5" pot.

DESCRIPTION OF THE PLANT

Of the commercial cultivars known to the inventor, the most similar in form, color, and habit to Pacific Isle are the cultivars Splendor and Hopscotch. Reference is made to Table I which compares certain characteristics of Pacific Isle to the same characteristics of the above mentioned cultivars. The comparisons shown in Table 1 represent side-by-side comparisons of the three Chrysanthemums grown under controlled conditions and with three applications of the growth regulator B-NINE TM at the rate of 2500 ppm. Comparisons were made during the month of November, 1993, in Encintas, Calif.

TABLE I

| CHARACTERISTIC | HOP-SCOTCH | PACIFIC ISLE | SPLENDOR |
|---|---|---|---|
| CAPITULUM FORM | Flat | Flat | Flat |
| CAPITULUM TYPE | Daisy | Daisy | Daisy |
| DIAMETER ACROSS FACE OF CAPITULUM | 7.5 cm | 11.6 cm | 12.2 cm |
| BRANCHING PATTERN | Upright and Spreading | Upright and Spreading | Upright and Spreading |
| BREAKS/PINCH | 4.4 | 4.0 | 4.0 |
| HEIGHT IN A 6.5" POT | 9.5–11.5 inches | 9.5–11.5 inches | 9.5–11.5 inches |
| DISC FLORET | Yellow | Yellow | Yellow |
| NO. DISC FLORETS | 183.2 | 200.4 | 133.8 |
| LENGTH OF DISC FLORETS | 0.64 cm | 0.7 cm | 0.6 cm |
| RAY FLORET COLOR | Front: Yellow 9A | Front: Lavender 62A–62B | Front: Purple 75A |

TABLE I-continued

| CHARACTERISTIC | HOP-SCOTCH | PACIFIC ISLE | SPLENDOR |
|---|---|---|---|
| | Back: Yellow 6A | Back: Lavender 62D | Back: Purple 75D |
| NO. RAY FLORETS | 32.6 | 94.2 | 52.3 |
| SHAPE OF RAY FLORETS | Elliptic | Elliptic | Elliptic |
| LENGTH OF RAY FLORETS | 3.85 cm | 5.1 cm | 5.2 cm |
| WIDTH OF RAY FLORETS | 1.43 cm | 1.5 cm | 1.5 cm |
| NUMBER OF FLOWER/BREAK | 6.7 | 4.6 | 10.6 |
| LEAF COLOR | Front: 147A Back: 147B | Front: 139A-B Back: 138A | Front: 139A Back: 138A |
| MATURE LEAF LENGTH | Up To 10.2 cm | Up To 8.3 cm | Up To 8.4 cm |
| MATURE LEAF WIDTH | 5.95 cm | 4.8 cm | 4.5 cm |
| RESPONSE: TREATMENT | 8.5 weeks: medium vigorous grower | 8.5 weeks: medium vigorous grower | 9.0 weeks: medium vigorous grower |

The three cultivars are similar in having a large flat, daisy capitulum. The diameter of the capitulum of Splender tends to be larger than the capitulum of Pacific Isle. Both Splendor and Pacific Isle tend to have larger diameter capitulums than Hopscotch. All three cultivars have similar upright, spreading branching patterns and a similar number of breaks per pinch per plant. The finished plant height and the color of the disc florets is also similar for the three cultivars. Pacific Isle tends to have more disc florets than either Hopscotch or Splendor. The length of the disc florets is similar for all three cultivars.

The front ray floret color for Pacific Isle is lavender 62A-62B for Hopscotch is yellow 9A; and for Splendor is purple 75A. The back ray floret color of Pacific Isle is lavender 62D; for Hopscotch is yellow 6A; and for Splendor is purple 75D. Pacific Isle has signficantly more ray florets than Splendor and Hopscotch. Splendor has more ray florets than Hopscotch. The ray florets of all three cultivars are elliptic. Pacific Isle has ray florets that are similar in length to Splendor. Hopscotch has shorter ray florets. The width of the ray florets is similar for all three cultivars. The colors of the leaves of Pacific Isle is similar to Splendor. Hopscotch has darker leaves than either of the other cultivars. Hopscotch has the longest mature leaf length. Pacific Isle and Splendor have similar leaf length. The three cultivars have similar leaf width. The response time from the start of short days in the same for Hopscotch and Pacific Isle at 8.5 weeks. Response time is slightly higher for Splendor, 9.0 weeks.

THE PLANT

Classification:

*Botanical.*—*Dendranthema grandiflora.*

*Cultivar name.*—Pacific Isle.

*Commercial.*—Flat daisy to grown primarily as a Spray/CBR (center bud removal) or disbud pot mum.

Inflorescence:

*Capitulum.*—Form: flat. Type: Daisy. Diameter across face: Average of 11.6 cm as a disbud.

Corolla of ray florets:

*General tonality from a distance of three meters-.*—lavender.

*Color.*—Front fully expanded outer ray floret: 62A-B. Back fully expanded outer ray floret: 62D. Disc floret color. Yellow.

General appearance:

*Height.*—When grown in a 6.5" pot with b 1-4 applications of B-NINE TM, the total plant height may be maintained between 9.5-11.5 inches.

*Branching pattern.*—Upright and spreading with an average of 4.0 breaks when grown with one pinch.

*Foliage.*—Color (upper surface): 139A-B. Color (lower surface): 138A. Shape: See photograph.

Reproductive organs:

*Androecium.*—Present in disc floret only: Pollen: scant.

*Gynoecium.*—Present in both ray and disc florets.

What is claimed is:

1. A new and distinct Chrysanthemum plant substantially as herein described and shown, characterized by its lavender ray floret coloration and exceptional upright to spreading habit.

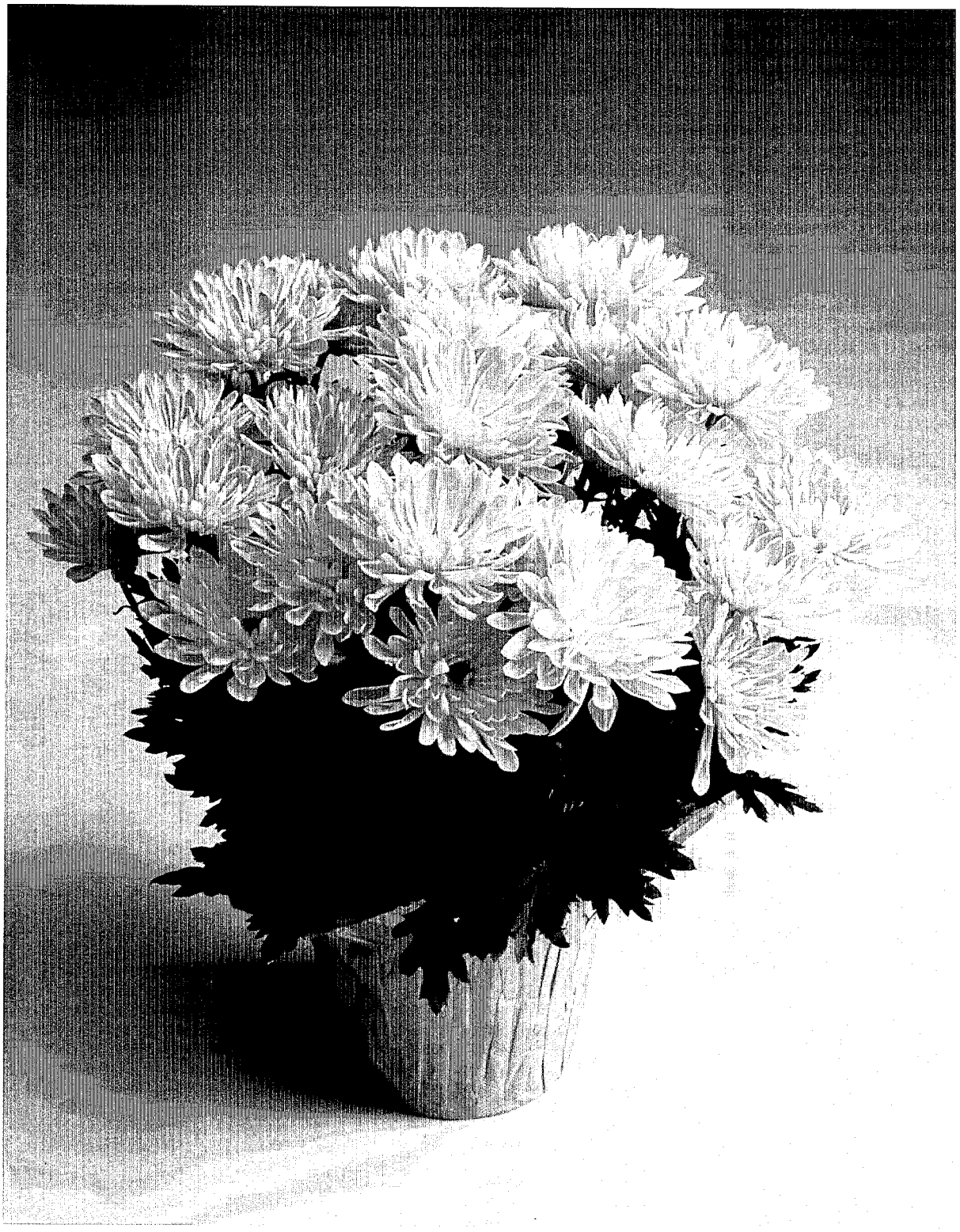

* * * * *